United States Patent [19]
>
> Yoshie et al.
>
> [11] Patent Number: 5,071,638
>
> [45] Date of Patent: Dec. 10, 1991

[54] SHAPE RETENTIVE ORAL COMPOSITION FOR DENTAL APPLICATIONS

[75] Inventors: Makoto Yoshie, Yokohama; Shinichi Seto, Tokyo; Fumito Takahashi, Sagamihara, all of Japan

[73] Assignee: Lion Corporation, Tokyo, Japan

[21] Appl. No.: 136,385

[22] Filed: Dec. 22, 1987

[30] Foreign Application Priority Data

Dec. 26, 1986 [JP] Japan ................................. 61-308522

[51] Int. Cl.$^5$ .......................... A61K 7/16; A61K 7/24
[52] U.S. Cl. ........................................ 424/49; 424/55; 424/57
[58] Field of Search ............................... 424/49, 55, 57

[56] References Cited

U.S. PATENT DOCUMENTS 3,689,637  9/1972  Pader .................................... 424/52
4,144,323  3/1979  Lamberti ............................... 424/49
4,172,121  10/1979  Calvin et al. ......................... 424/49

FOREIGN PATENT DOCUMENTS 2033678  6/1970  Fed. Rep. of Germany .
2409755  3/1974  Fed. Rep. of Germany .
60-75412  4/1985  Japan .

OTHER PUBLICATIONS

*Surface Chemistry,* Lloyd I. Osipow, Reinhold Publishing Corporation, N.Y. 1964, pp. 29-33.
Janistyn, "Handbuch Der Kosmetika...," 2nd ed., part 3: Die Korperpflegemittel, 1987, pp. 828-829.

*Primary Examiner*—Ronald W. Griffin
*Attorney, Agent, or Firm*—Birch, Stewart, Kolasch & Birch

[57] ABSTRACT

An oral composition containing (i) fumed silica and polyethylene glycol having an average molecular weight of 2000 to 6000.

8 Claims, No Drawings

SHAPE RETENTIVE ORAL COMPOSITION FOR DENTAL APPLICATIONS

BACKGROUND OF THE INVENTION

1. Field of the Invention

The present invention relates to an oral composition such as a dentifrice suitable for use in a vertical pump type container. More specifically, it relates to an oral composition having a good shape retentionability even when prepared as a low viscosity composition, having a good extrudability from a pump type container, and having an excellent feeling and taste when used.

2. Description of the Related Art

Recently, various vertical pump type containers capable of squeezing toothpaste therefrom only by pushing a press-operating portion such as a button have been proposed in, for example, Japanese Unexamined Utility Model Publication (Kokai) Nos. 54-34641 and 55-38783 and Japanese Unexamined Patent Publication Nos. 57-68367 and 57-68368, and it has been found that the use of toothpaste contained in such pump type containers is commercially viable. However, conventional toothpaste formulations are not suitable for use in such pump type containers, because toothpastes suitable for use in such pump type containers should preferably have a viscosity lower than that of conventional toothpastes, from the viewpoint of the structure of the container, so that the extrudability of the toothpastes from the container is made highly satisfactory. Furthermore, the toothpaste is required to have good shape retentionability when the toothpaste is placed on a toothbrush, even when the toothpaste has a low viscosity. However, although the shape retentionability of a dentifrice composition can be maintained by using a conventional thickener such as sodium carboxymethyl cellulose or carrageenan in conventional dentifrice compositions, the shape retentionability is still poor when the toothpaste has a low viscosity.

The present inventors have proposed, in Japanese Examined Patent Publication (Kokai) No. 60-75412, the provision of a toothpaste composition having a good shape retentionability when the viscosity is lowered to 600 poise or less, which is lower than the viscosities of conventional dentifrice compositions, by the addition of fumed ultra-fine amorphous silica.

Namely, the present inventors have proposed an effective realization of shape retentionability obtained by using a fumed ultra-fine amorphous silica in a dentifrice composition having a low viscosity, and thus obtained a suitable dentrifrice composition for use in a vertical pump type container.

In this connection, calcium phosphate, calcium carbonate, hydrated alumina, and silica type abrasives including precipitated silica are generally used as an abrasive base for conventional dentifrice compositions. However, when calcium phosphate, calcium carbonate, or hydrated alumina is used as an abrasive base in a dentifrice composition for a pump type container, the following problems arise:

(1) Since only a small amount of these abrasive bases can be formulated into the dentifrice composition, to maintain a good extrudability from a pump type container, the cleaning ability of the dentifrice composition is unsatisfactory.

(2) Since a binder such as sodium carboxymethyl cellulose in the composition causes gellation and coagulation by multivalent metal ions dissolved from the powder of the above-mentioned abrasive bases, the extrudability of the dentifrice composition from the container sometimes becomes poor. Accordingly, silica type abrasive bases are mainly used as a base in dentifrice compositions for pump type containers.

However, although the shape retentionability of such dentifrice compositions with a low viscosity for pump type containers can be improved to a certain extent by formulating fumed silica therein, the shape retentionability thereof is likely to be decreased when stored at a high temperature, and sure the extrudability thereof from the container largely depends upon the temperature, a poorer extrudability occurs when lowered temperature. Furthermore, when fumed silica is used for improving the shape retentionability in the dentifrice compositions, and when silica abrasive bases are used in the dentifrice compositions, the structural viscosity of the dentifrice composition is changed with the elapse of time and, when the composition is stored for a long term, the extrudability thereof becomes poor.

SUMMARY OF THE INVENTION

Accordingly, the objects of the present invention are to eliminate the above-mentioned disadvantages of the prior art and to provide an oral composition, especially a dentifrice composition, having a good shape retentionability even with a low viscosity and a good extrudability even at a low temperature, regardless of the temperature and the term during storage having an excellent taste and effect, and suitable for use in a pump type container.

Other objects and advantages of the present invention will be apparent from the following description.

In accordance with the present invention, there is provided an oral composition comprising (i) fumed silica and (ii) polyethylene glycol having an average molecular weight of 2000 to 6000.

DESCRIPTION OF THE PREFERRED EMBODIMENTS

The present inventors have studied ways in which to accomplish the above-mentioned objects, and as a result, found that, when fumed silica is used in combination with polyethylene glycol having an average molecular weight (i.e., number-average molecular weight) of 2000 to 6000, especially when 0.1% to 5% by weight, more preferably 0.3% to 3% by weight, based on the total amount of the composition, of fumed silica is used, in combination with 0.1% to 5% by weight, based on the total amount of the composition, of polyethylene glycol having an average molecular weight of 2000 to 6000, a desired oral composition having (1) an excellent shape retentionability when the oral composition is placed on, for example, a toothbrush, even at a viscosity lower than that of a conventional dentifrice composition, (2) exhibiting an excellent and stable extrudability from a pump type container, when stored in a pump type container, regardless of the temperature, e.g., without a poor extrusion at a low temperature or after long-term storage, and (3) having a good taste and effect, can be provided. Thus, the desired oral composition suitable for use in a pump type container can be successfully obtained by using fumed silica in combination with polyethylene glycol having an average molecular weight of 2000 to 6000.

It is known in the art that polyethylene glycol is used as a humectant in oral compositions (see Japanese Unexamined Patent Publication (i.e., Kokai) Nos. 47-10250, 49-75741, 50-58244, 56-97217, and 58-126806), and that a dentifrice composition containing fumed silica is suitable as a dentifrice composition for a pump type container (see Japanese Unexamined Patent Publication (Kokai) No. 60-75412. However, there are no teaching in the prior art that, when an appropriate amount of fumed silica is formulated, in combination with an appropriate amount of polyethylene glycol having an average molecular weight of 2000 to 6000, into an oral composition as mentioned above, the desired oral composition having an excellent shape retentionability and extrudability, regardless of the temperature and even when prepared with a low viscosity, can be obtained, and when silica type abrasives such as abrasive precipitated silica are formulated as an abrasive base into the oral compositions, the changes in the structural viscosity of the silica type abrasives and the fumed silica formulated into the oral compositions, and the occurrence of a poor extrudability from a pump type container after a long-term storage in the container or insufficient extrusion from a pump type container at a low temperature, can be prevented to a great extent. Therefore, it is newly found by the present inventors that the oral compositions containing fumed silica in combination with polyethylene glycol having an average molecular weight of 2000 to 6000 formulated thereinto have a sufficient shape retentionability on a toothbrush and extrudability from the container when stored in a vertical pump type container.

The oral compositions according to the present invention can be preferably utilized as dentifrice compositions which can be prepared from abrasives, humectants, binders, thickeners, and optionally, surfactants, sweeteners, flavors, preservatives, various effective components, and other optional additives, wherein fumed silica is used as a thickener according to the present invention.

The fumed silica is preferably formulated in an amount of 0.3 to 5% (i.e., "% by weight", as also hereinbelow) more preferably 1 to 3%, based on the total amount of the composition. When the formulation amount of the fumed silica is less than 0.3% by weight, the shape retentionability becomes unsatisfactory. Conversely, when the amount is more than 5%, the taste and texture when used are sometimes reduced.

The fumed silica usable in the present invention can be selected from various types of fumed silica. The fumed silica preferably used is fumed ultra-fine amorphous silica having an average particle size of the primary particle of 5 to 40 nm, especially 8 to 20 nm. Of these types of fumed ultra-fine amorphous silica, those having a specific surface area of 50 to 400 m$^2$/g, as measured by the BET absorption method with nitrogen, an apparent specific gravity of 40 to 120 gl, and an oil absorption amount of 3 ml/g or more, are preferably used in the present invention. Examples of such fumed silica are commercially available silica such as Aerosil ® (manufactured by Degussa) and Cab-O-Sil ® (manufactured by Cabot).

Furthermore, in the present oral composition, polyethylene glycol having an average molecular weight of 2000 to 6000 is used together with the fumed silica, as mentioned above. Thus, in the present invention, by using the fumed silica in combination with the polyethylene glycol having an average molecular weight of 2000 to 6000, the desired oral composition having an excellent shape retentionability on a toothbrush without deforming even when prepared at a lower viscosity, compared to conventional oral compositions, and having a good extrudability when contained in, for example, a pump type container, regardless of the temperature and without an insufficient extrusion from the container at a low temperature, can be obtained. Furthermore, the occurrences of changes in the structural viscosity with the elapse of the time due to the use of the fumed silica contained in the composition, and due to the use of silica type abrasives such as abrasive precipitated silica, and the occurrence of a poor extrudability of the oral composition contained in a container after a long-term storage, can be prevented to a great extent, and the desired oral composition having a good extrudability even after a long-term storage and a good taste and texture when used, can be obtained.

In the present invention, as the polyethylene glycol, those having an average molecular weight of 2000 to 6000 are used. When the polyethylene glycol having an average molecular weight of less than 2000 is used, the shape retentionability of the composition is decreased and the extrudability of the composition at a lowered temperature decreased. Conversely, when the average molecular weight is larger than 6000, the application taste and texture is decreased.

Furthermore, the present oral composition preferably contains preferably 0.1 to 5%, more preferably 0.3 to 3%, based on the total weight of the composition, of polyethylene glycol having the above-mentioned molecular weight. When the amount of the polyethylene glycol in the formulation is less than 0.1%, the shape retentionability is decreased. Conversely, when the amount of the polyethylene glycol is more than 5%, the application feeling and effect is decreased.

When the fumed silica and the polyethylene glycol having an average molecular weight of 2000 to 6000 are formulated, the weight ratio of the fumed silica/ the polyethylene glycol is preferably 50/1 to 1/5.

Examples of the binders usable in the present invention are cellulose derivatives such as alkali metal salts of carboxymethyl cellulose, methyl cellulose, hydroxyethyl cellulose, and sodium carboxymethyl hydroxyethyl cellulose; alkali metal alginates such as sodium alginate; propylene glycol esters of alginic acid; gums such as carrageenan, xanthan gum, tragacanth gum, karaya gum, and gum arabic; synthetic binders such as polyvinyl alcohol, sodium polyacrylate, carboxyvinyl polymer, and polyvinyl pyrrolidone; and inorganic binders such as aluminum silicate gel and LAPONITE ®. These binders may be used alone or in any mixture thereof. The amount in the formulation is generally 0.5 to 5% in the total composition.

Example of the humectants usable in the present invention are sorbitol, glycerol, ethylene glycol, propylene glycol, 1,3-butylene glycol, polypropylene glycol, xylitol, maltitol, and lactitol and polyethylene glycol having an average molecular weight of 200 to 1500. These humectants may be used alone or in any mixture thereof. The formulation amount is generally 10 to 75%.

The oral compositions according to the present invention further contain abrasives and others components, depending upon, for example, the types thereof. Examples of the abrasives are dicalcium phosphate dihydrate and anhydride, monocalcium phosphate (monobasic), tricalcium phosphate, calcium carbonate, calcium pyrophosphate, calcium sulfate, titanium dioxide, alumina, hydrated alumina, silica type abrasives (e.g., precipitated silica and anhydrous alkali metal silicate complexes), aluminum silicate, insoluble sodium metaphosphate, magnesium phosphate (tribasic), magnesium carbonate, bentonite, zirconium silicate, and synthetic resins. These abrasives may be used alone or in any mixture. The formulation amount of the abrasives is generally 0 to 50%, especially 10 to 30%.

Examples of the silica type abrasives are those disclosed in, for example, Japanese Unexamined Patent Publication (Kokai) Nos. 49-91994 (corresponds to U.S. Pat. No. 3,898,840), 49-94712 (corresponds to U.S. Pat. No. 4,076,549 and U.S. Pat. No. 4,105,757), 50-64198 and 49-91994, 49-94712, 50-64198, 50-65497 (both corresponding to U.S. Pat. No. 3,960,586 and U.S. Pat. No. 4,122,161), 51-128695, 51-136841 (corresponding to U.S. Pat. No. 4,132,806 and U.S. Pat. No. 4,167,920), and Japanese Examined Patent Publication (Kokoku) 54-4919 50-65497, 51-128695, 51-136841, and 54-4919. More specifically, precipitated silica, silica xerogel, silica aerogel having a primary particle size of 500 nm or less and a secondary particle size of 1 to 30 μm, such as commercially available Zeodent ®, ZeO ®, Sident ®, and Syloid ®(all Trade Marks), are preferably used in the present invention. Of these abrasives, precipitated silica is especially preferably used. Especially, precipitated silica having an $SiO_2$ content of 70% or more, preferably 90% or more, an alkali metal or alkaline earth metal oxide content of 0 to 5%, a bonding amount of oxides of metals, such as aluminum, zirconium, magnesium, and calcium, to $SiO_2$ of 0 to 10%, preferably 0 to 5%, an adhered water content (i.e., loss on drying) of 1 to 10%, an average partial size weight of 0.5 to 30 μm, preferably 1 to 15 μm, a specific surface area, measured by a BET method with nitrogen, of 500 $m^2/g$ or less, preferably 300 $m^2/g$ or less, a refractive index of 1.44 to 1.47, and an absorption amount of 0.6 to 1.3 cc/g, are preferably used. Specifically, examples of commercially available products usable in the present invention are ZeO 49 and Zeodent 113 from Huber (U.S.A.), Syloid AL-1, 63, 74, and 404 from W.R. Grace (U.S.A.), Neosyl ET from J. Crossfield & Sons (U.S.A.), Sident 3, 12, and 20 from Degussa (West Germany), and zircono silicate from Taki Chemical (Japan). These silica type abrasives are preferably used in the present invention.

The present oral compositions may further contain, as an optional components, surfactants such as anionic surfactants, for example, water-soluble salts of long-chained alkyl sulfate esters having an alkyl group with 8 to 18 carbon atoms such as sodium lauryl sulfate and sodium myristyl sulfate; water-soluble long-chained fatty acid monoglyceride monosulfate such as sodium hydrogenated coconut fatty acid monoglyceride monosulfate; alkyl aryl sulfonate such as sodium dodecylbenzene sulfonate; long-chained alkyl sulfonate; long-chained fatty acid esters of 1,2-dihydroxy propane sulfonates; substantially saturated long-chained aliphatic acylamides of aliphatic amino carboxylic acid compounds such as sodium, potassium or ethanolamine salts of N-lauroyl, N-myristoyl or N-palmitoyl sarcosine; nonionic surfactants such as sucrose fatty acid esters having a fatty acid group with 12 to 18 carbon atoms such as sucrose mono and dilaurates; lactose fatty acid esters; lactitol fatty acid esters; maltitol fatty acid esters; stearic acid monoglyceride; condensation products of polyethylene oxide with fatty acids, aliphatic alcohols, polyols and polypropylene oxide such as polyoxyethylene sorbitan monolaurate, polyoxyethylene sorbitan monostearate, polyoxyethylene (10, 20, 40, 60, 80, 100 mol) hydrogenated castor oil, polymerization products of ethylene oxide and propylene oxide and polyoxyethylene polyoxypropylene monolauryl esters; and amphoteric surfactants such as betaine type and amino acid type surfactants. These surfactants may be used alone, or in any mixture thereof, in an amount of, for example, 0 to 7%, preferably 0.5 to 5%.

Furthermore, sweeteners such as saccharin sodium, stebiocide, neohesperidyl dihydrochalcon, glycyrrhizin, perillartine, thaumatin, asparatylphenyl alamine methyl ester, p-methoxy cinnamic aldehyde, sucrose, lactose, fructose, and sodium cyclamate. These sweeteners may be used alone, or in any mixture thereof, in an amount of 0 to 1%, preferably 0.01 to 0.5%. Furthermore, if desired, preservatives such as methyl, ethyl, sipyl, and butyl p-hydroxy benzoates sodium benzoate, and monoglycerides of lower fatty acids; flavors such as winter green oil, spearmint oil, peppermint oil, sassafras oil, clove oil, and eucalyptus oil; brightening agents such as gelatin, peptone, alginine hydrochloride, albumin, casein, and titanium dioxide; silicone; coloring agents; and other conventional additives, may be used.

The present oral compositions may further optionally contain effective components such as allantoin, ε-aminocaproic acid, tranexamic acid, enzymes such as dextranase, amylase, protease, mutanase, lysozyme, lisokinase, and lytic enzyme; alkali metal monofluoro phosphates such as sodium monofluorophosphate and potassium monofluoro phosphate, fluorides such as sodium fluoride, ammonium fluoride, stannous fluoride; chlorohexidine salts, dihydrocholesterols, glycyrrhizin salts, glycyrrhetic acid, glycerophosphate, chlorophyll, caro peptide, water-soluble inorganic phosphoric compounds, vitamins, antitartar, bactericides; and plaque inhibiting agents. These effective components may be used alone or in any mixture thereof.

The present oral composition may be prepared by formulating the above-mentioned fumed silica and the above-mentioned polyethylene glycol having an average molecular weight of 2000 to 6000 together with the above-mentioned appropriate and optional components. The preferable viscosity of the present oral composition is 800 poise or less, more preferably 300 to 700 poise. The resultant oral composition according to the present invention has an excellent extrudability and shape retentionability even in a low viscosity. Thus, the present oral composition is suitably for use in a pump type container. The oral composition in the container is emitted from the outlet of the container by pushing or pressing an extrusion operating means (e.g., a push button).

The present oral composition can be advantageously utilized in the pump type containers disclosed in, for example, Japanese Unexamined Utility Model Publication Nos. 54-34641, 55-38783, 56-46572, 56-100378, 56-121677, 57-44041, 57-74168, and 57-164079 and Japanese Unexamined Patent Publication (Kokai) Nos. 57-68367 and 57-68368.

As explained hereinabove, and further explained hereinbelow, the present oral compositions have (1) a good shape retentionability even when prepared in a low viscosity, (2) a good extrudability from a pump type container without an insufficient extrusion at a lowered temperature and without a poor extrusion after long-term storage, and (3) an excellent textures when used. Thus, the present oral compositions are suitable for use in a vertical pump type container.

EXAMPLES

The present invention will now be further illustrated by, but is by no means limited to, the following Experiment and Examples.

Experiment

Toothpaste composition Nos. 1 to 9 listed in Table 1 were prepared according to the following formulation, and the effects of the thickening fumed silica and thickening precipitated silica were compared, and the effects of the silica in combination with polyethylene glycol were evaluated.

| Formulation | Amount (wt. %) |
|---|---|
| Polyethylene glycol (PEG) having an average molecular weight listed on Table 1 | see Table 1 |
| Fumed silica (Aerosil 200) | see Table 1 |
| Precipitated silica (Syloid 244) | see Table 1 |
| Abrasive silica anhydride having a particle size of 5 μm (Zeo 49) | 25 |
| 60% Sorbitol | 50 |
| Sodium carboxymethyl cellulose | 1.5 |
| Sodium saccharin | 0.2 |
| Sodium lauryl sulfate | 1.5 |
| Flavor | 1.0 |
| Methyl parahydroxybenzoate | 0.2 |
| Water | Balance |
| Total | 100.0 wt. % |

The properties of the fumed silica (Aerosil 200) and the precipitated silica (Syloid 244) are as follows:

|  | Aerosil 200 | Syloid 244 |
|---|---|---|
| Primary particle size | 16 mμ | 11 mμ |
| Specific surface area | 200 m²/g | 300 m²/g |
| Bulk density | 50 g/l | 150 g/l |

The viscosities of the toothpaste compositions obtained were determined, immediately after preparation, at a temperature of 25° C. by a Brook field type viscometer. Furthermore, the shape retentionability, extrudability, and feeling and taste when used were evaluated by filling the toothpaste compositions into a pump type container disclosed in Japanese Unexamined Utility Model Publication No. 54-34641, followed by emitting therefrom, under the following evaluation criteria.

EVALUATION CRITERIA

Shape Retentionability

○: Placed in good condition on toothbrush and no substantial deformation of shape
Δ: Minor deformation
x: Easily flows on toothbrush

Extrudability

○: Extruded smoothly from container with no substantial resistance
Δ: Extruded from container with some resistance
x: Difficult to extrude from container, and remarkable resistance

Taste and Texture When Used

The taste and texture of toothpastes when used were evaluated by a panel consisting of 20 members.
○: Good taste and texture during use
Δ: Fair taste and texture during use
x: Poor taste and texture during use
The results are shown in Table 1.

TABLE 1

| Component | No. 1*2 | No. 2*2 | No. 3*2 | No. 4*1 | No. 5*1 | No. 6*1 | No. 7*2 | No. 8*2 | (wt. %) No. 9*2 |
|---|---|---|---|---|---|---|---|---|---|
| Polyethylene glycol 400 | — | 4 | — | — | — | — | — | — | — |
| Polyethylene glycol 1000 | — | — | 2 | — | — | — | — | — | — |
| Polyethylene glycol 2000 | — | — | — | 2 | — | — | — | — | — |
| Polyethylene glycol 4000 | — | — | — | — | 1 | — | — | 1 | 1 |
| Polyethylene glycol 6000 | — | — | — | — | — | 1 | — | — | — |
| Polyethylene glycol 11000 | — | — | — | — | — | — | 1 | — | — |
| Fumed silica (Aerosil 200) | 5 | 3 | 2 | 2 | 2 | 2 | 2 | — | — |
| Precipitated silica (Syloid 244) | — | — | — | — | — | — | — | 10 | — |
| Viscosity (poise) | 540 | 650 | 590 | 620 | 570 | 640 | 650 | 560 | 150 |
| Shape retentionability | Δ-x | Δ | Δ | ○ | ○ | ○ | ○ | x | x |
| Extrudability kept at low temperature (−5° C.) | x | x-Δ | Δ | ○ | ○ | ○ | ○ | x | ○ |
| stored at 50° C., 1 month storage | x | Δ | Δ | ○ | ○ | ○ | ○ | x | ○ |
| Taste and Texture when used | x-Δ | ○ | ○ | ○ | ○ | ○ | x-Δ | Δ | ○ |

*1 Present Invention
*2 Comparative

As is clear from the results shown in Table 1, the toothpaste compositions containing the fumed silica in combination with the polyethylene glycol having an average molecular weight of 2000 to 6000 have a good shape retentionability even when prepared with a low vicosity of 700 poise or less, and a good extrudability even with a low temperature and even after storing at a high temperature, and further have a good taste and texture.

In the following Examples, the viscosity was measured at a temperature of 25° C. by a Brook field type viscometer.

EXAMPLE 1

| Ingredient | wt. % |
|---|---|
| Silicic anhydride (Zeodent 113) | 25 |
| Glycerol | 10 |
| Sorbitol solution (60%) | 30 |
| Propylene glycol | 3 |
| Polyethylene glycol 4000 | 0.3 |
| Sodium carboxymethyl cellulose | 1.5 |
| Tranexamic acid | 0.05 |
| Fumed silica (Aerosil 200) | 2.0 |
| Sodium saccharin | 0.2 |
| Methyl parahydroxybenzoate | 0.15 |

-continued

| Ingredient | wt. % |
|---|---|
| Flavor | 1.0 |
| Sodium laurylsulfate | 1.5 |
| Purified water | Balance |
| Total | 100.0 wt. % |
| Viscosity | 580 poise |
| pH | 6.1 |

EXAMPLE 2

| Ingredient | wt. % |
|---|---|
| Silicic anhydride | 20 |
| Sorbitol liquid | 50 |
| Polyethylene glycol 400 | 4 |
| Polyethylene glycol 2000 | 3.0 |
| Carrageanan | 1.2 |
| Sodium monofluoro phosphate | 0.76 |
| Fumed silica (Aerosil 380) | 2.5 |
| Sodium saccharin | 0.2 |
| Methyl parahydroxybenzoate | 0.1 |
| Flavor | 1.0 |
| Sodium laurylsulfate | 1.8 |
| Lauroyl diethanolamide | 0.3 |
| Purified water | Balance |
| Total | 100.0 wt. % |
| Viscosity | 620 poise |
| pH | 6.5 |

EXAMPLE 3

| Ingredient | wt. % |
|---|---|
| Dicalcium phosphate | 30 |
| Glycerol | 5 |
| Sorbitol Solution (60%) | 40 |
| Propylene glycol | 2.5 |
| Polyethylene glycol 4000 | 0.5 |
| Carrageanan | 0.6 |
| Sodium polyacrylate | 0.7 |
| Glycyrrhetinic acid | 0.1 |
| Fumed silica (Cab-O-Sil M-5) | 1.5 |
| Sodium saccharin | 0.1 |
| Methyl parahydroxybenzoate | 0.15 |
| Flavor | 1.0 |
| Sodium lauryl sulfate | 1.5 |
| Purified water | Balance |
| Total | 100.0 wt. % |
| Viscosity | 450 poise |
| pH | 7.2 |

EXAMPLE 4

| Ingredient | wt. % |
|---|---|
| Zircono silicate (Taki Chemical Co.) | 17 |
| Sorbitol solution (60%) | 50 |
| Polyethylene glycol 4000 | 1.0 |
| Sodium carboxymethyl cellulose | 0.6 |
| Sodium polyacrylate | 0.5 |
| Chlorohexidine hydrochloride | 0.01 |
| Fumed silica (Aerosil 300) | 3.0 |
| Sodium saccharin | 0.1 |
| Methyl parahydroxybenzoate | 0.2 |
| Flavor | 1.0 |
| Sodium laurylsulfate | 1.0 |
| Sodium lauroyl sarcosinate | 0.5 |
| Lauroyl diethanolamide | 0.5 |
| Purified water | Balance |
| Total | 100.0 wt. % |
| Viscosity | 500 poise |
| pH | 6.8 |

EXAMPLE 5

| Ingredient | wt. % |
|---|---|
| Zircono silicate (Taki Chemical Co.) | 25 |
| Glycerol | 15 |
| Sorbitol liquid | 15 |
| Propylene glycol | 3 |
| Polyethylene glycol 6000 | 2.0 |
| Sodium alginate | 1.5 |
| Sodium monofluorophosphate | 0.76 |
| Tocopherol acetate | 0.2 |
| Fumed silica (Cab-O-Sil EH-5) | 2.5 |
| Saccharin sodium | 0.2 |
| Sodium benzoate | 0.5 |
| Flavor | 1.0 |
| Sodium laurylsulfate | 1.5 |
| Lauroyl diethanolamide | 0.2 |
| Purified water | Balance |
| Total | 100.0 wt. % |
| Viscosity | 550 poise |
| pH | 6.5 |

EXAMPLE 6

| Ingredient | wt. % |
|---|---|
| Calcium carbonate | 25 |
| Sorbitol liquid | 40 |
| Polyethylene glycol 2000 | 3.0 |
| Sodium polyacrylate | 1.5 |
| Tranexamic acid | 0.05 |
| Fumed silica (Cab-O-Sil M-7) | 2.0 |
| Saccharin sodium | 0.2 |
| Methyl parahydroxybenzoate | 0.2 |
| Flavor | 1.0 |
| Sodium laurylsulfate | 1.3 |
| Sodium lauroylsarcosinate | 0.3 |
| Purified water | Balance |
| Total | 100.0 wt. % |
| Viscosity | 700 poise |
| pH | 7.9 |

EXAMPLE 7

| Ingredient | wt. % |
|---|---|
| Silicic anhydride (Syloid 63) | 20 |
| Sorbitol liquid | 60 |
| Polyethylene glycol 2000 | 5.0 |
| Sodium carboxymethyl cellulose | 1.0 |
| Dextranase | 2000 u/g |
| Fumed silica (Cab-O-Sil MS-75) | 1.5 |
| Saccharin sodium | 0.1 |
| Methyl parahydroxybenzoate | 0.15 |
| Flavor | 1.0 |
| Sodium laurylsulfate | 1.8 |
| Myristoyl diethanolamide | 0.5 |
| Purified water | Balance |
| Total | 100.0 wt. % |
| Viscosity | 400 poise |
| pH | 5.9 |

EXAMPLE 8

| Ingredient | wt. % |
|---|---|
| Silicic anhydride (Zeodent 113) | 20 |
| Glycerol | 10 |
| Sorbitol solution (60%) | 30 |
| Propylene glycol | 2 |
| Polyethylene glycol 4000 | 2.0 |
| Sodium carboxymethyl cellulose | 0.5 |
| Carrageanan | 0.7 |

-continued

| Ingredient | wt. % |
|---|---|
| Sodium monofluorophosphate | 0.76 |
| Fumed silica (Aerosil 130) | 2.3 |
| Sodium saccharin | 0.1 |
| Methyl parahydroxybenzoate | 0.1 |
| Sodium benzoate | 0.5 |
| Flavor | 1.0 |
| Sodium laurylsulfate | 1.5 |
| Lauroyl diethanolamide | 1.0 |
| Purified water | Balance |
| Total | 100.0 wt. % |
| Viscosity | 650 poise |
| pH | 6.3 |

EXAMPLE 9

| Ingredient | wt. % |
|---|---|
| Silicic anhydride (Zeo 49) | 25 |
| Glycerol | 30 |
| Propylene glycol | 2 |
| Polyethylene glycol 6000 | 0.5 |
| Sodium carboxymethyl cellulose | 0.8 |
| Sodium alginate | 0.5 |
| Chlorohexidine hydrochloride | 0.01 |
| Tocopherol acetate | 0.2 |
| Fumed silica (Aerosil 200) | 2.1 |
| Sodium saccharin | 0.2 |
| Methyl parahydroxybenzoate | 0.1 |
| Sodium benzoate | 0.2 |
| Flavor | 1.0 |
| Sodium laurylsulfate | 1.2 |
| Sodium lauroylsarcosinate | 0.3 |
| Purified water | Balance |
| Total | 100.0 wt. % |
| Viscosity | 600 poise |
| pH | 6.0 |

EXAMPLES 10 and 11

| Ingredient | wt. % Example 10 | wt. % Example 11 |
|---|---|---|
| Zirconosilicate | 20 | 23 |
| Aluminosilicate | 5 | — |
| Glycerol | 5 | — |
| Sorbitol solution | 30 | 45 |
| Propylene glycol | 3 | — |
| Polyethylene glycol 400 | — | 4 |
| Polyethylene glycol 4000 | 0.5 | 1.0 |
| Sodium carboxymethyl cellulose | 0.7 | 1.2 |
| Carrageanan | 0.5 | — |
| Sodium monofluorophosphate | 0.76 | 0.76 |
| Chlorohexidine gluconate | 0.05 | — |
| Hexametaphosphoric acid | — | 1 |
| Fumed silica (Aerosil) | 2.5 | 2 |
| Sodium saccharin | 0.1 | 0.1 |
| Methyl parahydroxybenzoate | 0.2 | 0.1 |
| Sodium benzoate | 0.3 | 0.5 |
| Flavor | 1.0 | 1.0 |
| Sodium laurylsulfate | 1.5 | 1.8 |
| Lauroyl diethanolamide | 0.3 | 0.5 |
| Purified water | Balance | Balance |
| Total | 100.0 wt. % | 100.0 wt. % |
| Viscosity | 650 | 700 |
| pH | 6.5 | 6.3 |

The above-prepared dentifrice compositions of Examples 1 to 11 all had a good shape retentionability and extrudability when used in a pump type container, and had an excellent feeling and taste when used.

We claim:

1. A dentifrice composition comprising (i) fumed silica, (ii) precipitated silica and (iii) polyethylene glycol having an average molecular weight of 2000 to 6000, the weight ratio of the fumed silica tot eh polyethylene glycol being 50:1 to 1:5 and the weight ratio of the precipitated silicon to the polyethylene glycol being 25:0.3 to 20:3.

2. A dentifrice composition as claimed in claim 1, wherein the amount of the fumed silica in the total composition is 0.3% to 5% by weight and the amount of the polyethylene glycol having an average molecular weight of 2000 to 6000 in the total composition is 0.1% to 5% by weight.

3. A dentifrice composition as claimed in claim 2, wherein the amount of the fumed silica in the total composition is 1% to 3% by weight.

4. A dentifrice composition as claimed in claim 1, wherein the primary particle size of the fumed silica is 5 to 40 nm and the specific surface area of the fumed silica is 50 to 400 m$^2$/g measured by a BET method with nitrogen.

5. A dentifrice composition as claimed in claim 1, wherein the viscosity of the composition is 300 to 700 poise.

6. A dentifrice composition as claimed in claim 4, wherein the amount of the fumed silica in the total composition is 1% to 3% by weight.

7. A dentifrice composition as claimed in claim 4, wherein the primary particle size of the fumed silica is 8 to 20 nm.

8. A dentifrice composition as claimed in claim 1, wherein the amount of the polyethylene glycol having an average molecular weight of 2000 to 6000 in the total composition is 0.3 to 3% by weight.

* * * * *

UNITED STATES PATENT AND TRADEMARK OFFICE
CERTIFICATE OF CORRECTION

PATENT NO. : 5,071,638

DATED : December 10, 1991

INVENTOR(S) : Makoto YOSHIE, Shinichi SETO, and Fumito TAKAHASHI

It is certified that error appears in the above-identified patent and that said Letters Patent is hereby corrected as shown below:

Column 12, line 24 (in Claim 1), the phrase "tot eh" should read --to the--; and line 26, the term "silicon" should read --silica--.

Signed and Sealed this

Twenty-third Day of February, 1993

Attest:

STEPHEN G. KUNIN

*Attesting Officer*   *Acting Commissioner of Patents and Trademarks*